United States Patent [19]

Knifton

[11] Patent Number: 5,300,703
[45] Date of Patent: Apr. 5, 1994

[54] ALKYLPHENOL SYNTHESIS USING HETEROPOLY ACID CATALYSTS

[75] Inventor: John F. Knifton, Austin, Tex.

[73] Assignee: Texaco Chemical Company, White Plains, N.Y.

[21] Appl. No.: 43,091

[22] Filed: Apr. 5, 1993

[51] Int. Cl.$^5$ .............................. C07C 37/14
[52] U.S. Cl. .................... 568/794; 568/791
[58] Field of Search ............... 568/786, 789, 791, 794

[56] References Cited

U.S. PATENT DOCUMENTS

| | | | |
|---|---|---|---|
| 4,568,778 | 2/1986 | Imanari et al. | 568/789 |
| 4,912,264 | 3/1990 | Takeshita et al. | 568/794 |
| 5,059,727 | 10/1991 | Ito | 568/794 |
| 5,171,896 | 12/1992 | Knifton et al. | 568/794 |
| 5,175,375 | 12/1992 | Chang et al. | 568/794 |

OTHER PUBLICATIONS

K. Nowinska et al, J. Chem. Soc. Faraday Trans.; vol. 87, p. 749 (1991).

*Primary Examiner*—James H. Reamer
*Attorney, Agent, or Firm*—James L. Bailey; Kenneth R. Priem; Cynthia L. Kendrick

[57] ABSTRACT

Disclosed is a one step method for synthesis of alkylphenols which comprises reacting phenol with the corresponding olefin under adiabatic conditions in the presence of a catalyst comprising a heteropoly acid represented by the structure:

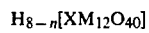

$$H_{8-n}[XM_{12}O_{40}]$$

where $x = P$ or Si, $M = Mo$ or $w_v$ and $n$ is an integer which is 4 or 5, alone, or deposited on an inert support, at a temperature of from 60° C. to 250° C. and a pressure of from near atmospheric to about 500 psi.

7 Claims, No Drawings

ALKYLPHENOL SYNTHESIS USING HETEROPOLY ACID CATALYSTS

BACKGROUND OF THE INVENTION

1. Field Of The Invention

The invention relates to a one step method for the preparation of alkylphenols from phenol and the corresponding olefin. More particularly it relates to a one-step method for preparation of alkyl phenols by reacting phenols and the corresponding olefins over a catalyst comprising a heteropoly acid, homogeneous or deposited on a support. The method is especially effective in the synthesis of the most desirable para-alkyl phenol, para-nonylphenol, from phenol and nonene.

2. Description Of The Related Art

It is known in the art to prepare higher molecular weight alkylphenols, such as p-tert-octylphenol, p-nonylphenol and dodecylphenol by alkylating phenol with diisobutylene, propylene trimer and propylene tetramer, respectively, under acidic conditions. Nonylphenol, in particular, is used as an intermediate for surfactants, as well as antioxidants and in lube oil additives.

In "Bisphenol A and Alkylated Phenols", SRI PEP Report No. 192 (Dec. 1988)., page 4—4, it is reported that it is known in the art to prepare various alkylphenols by acid catalyzed reactions of phenols with various olefins. These alkylphenols may include p-tert-butylphenol, p-isopropylphenol, p-sec-butylphenol, p-tert-octylphenol, nonylphenol and dodecylphenol. The alkylation reaction takes place at or near atmospheric pressure in the presence of an acidic catalyst such as a mineral acid, a Lewis acid (e.g. boron trifluoride) or a cation exchange resin (e.g. styrene-divinyl benzene resin). The acid catalysts lead to predominantly para-alkylated phenol when the para position is available. Generally a molar ratio of phenol to olefin of 1.5-3:1 is desired to minimize the yield of dialkylphenols.

U.S. Pat. No. 4,198,531, to BASF, discloses a process for continuous manufacture of p-alkylphenols by reacting phenol with olefin at 70°-140° C. in a fixed bed of an organic sulfonic acid cation exchange resin.

A Lewis acid or Bronsted acid catalyst is employed in U.S. Pat. No. 4,096,209 to Ciba-Geigy to prepare a phosphorylated butylated phenol/phenol ester mixture.

In U.S. Pat. No. 2,684,389 to Gulf R & D a phenol and monoolefin are mixed in the presence of a silica-aluminum adsorbent catalyst at 137° C. A silica-alumina catalyst is also employed in U.S. Pat. No. 3,876,710 to Hitachi to produce PTBP from phenol and isobutylene.

A BF$_3$ catalyst is used for of phenol and isobutene in British Patent 1,294,781 to Hoechst where the product cooled to form crystals which are crushed before ammonia is added to remove the catalyst. British Patent 1,249,571 is related.

In German Offen. 3,443,736 to Huels the catalyst is a sulfonated polystyrene ion exchange catalyst. U.S. Pat. No. 4,461,916, also to Huels, discloses a two-stage approach for producing p-tert-octylphenol using an acid ion exchange resin. U.S. Pat. No. 4,236,033 and U.S. Pat. No. 4,168,390 to Huels also disclose ion exchange resins, the latter comprising a LEWATIT ® resin deactivated with Al$_2$(SO$_4$)$_3$.

British Patent 2,120,953 to ICI discloses a process for producing nonylphenol by reacting diisobutene with phenol in the presence of a catalyst comprising fuller's earth with alkyl or aryl phosphate or phosphate ester.

U.S. Pat. No. 3,872,173 to Progil discloses the reaction of gaseous isobutene with liquid phenol in the presence of an acid-activated clay, again in two steps.

A highly acidic aryl sulfonic acid catalyst is employed in U.S. Pat. No. 3,932,537 to react phenol with isobutene under anhydrous conditions.

U.S. Pat. No. 3,422,157 to Union Carbide employs a cation exchange resin catalyst.

British Patent 1,314,623 to Union Rheinische Braunkohlen discloses an activated, acid-free, bleaching earth catalyst.

In U.S. Pat. No. 4,260,833, to UOP, phenol and isobutylene are reacted at 250° C. in the presence of a lithiated alumina catalyst. U.S. 3,929,912 discloses a more general alkylation of phenol and olefins in the presence of hydrogen fluoride and carbon dioxide.

An aluminum phenoxide catalyst is used for the orthoalkylation of phenol with butene-1 in French Patent 2,296,610, and U.S. Pat. No. 3,766,276, to Ethyl, as well as U.S. Pat. No. 3,933,927.

A boron trifluoride catalyst is used for the alkylation of phenol in U.S. Pat. No. 3,317,612.

Activated earth and phosphoric acid are used in a liquid phase transalkylation process in British Patent 1,444,935.

Acids are also useful for the condensation of phenol with acetone. Representative acids include an aromatic sulfonic acid (German Offen. 2,811,182 and U.S. Pat. No. 4,387,251), a volatile acid catalyst (U.S. Pat. No. 2,623,908), a strong mineral acid such as HCl or H$_2$SO$_4$ (U.S. Pat. No. 2,359,242), hydrochloric acid (U.S. Pat. No. 4,517,387), H$_2$SO$_4$ or HCl and 2-(4-pyridyl)ethanethiol (Japanese Kokai 57-118528), concentrated HCl (Japanese Kokai 60-38335) and hydrogen chloride (U.S. Pat. No. 4,169,211).

Of the known processes for producing alkylphenols, generally the processes require two stages for cooling and recycling and many of the catalysts are not stable at high temperatures. In addition, it is often difficult to obtain high para- to ortho- ratios or to obtain, (in the case of nonylphenol synthesis) more mononylphenol relative to dinonylphenol, while from the art it would appear that conversions of about 80% are about the most which could be expected in any process to prepare alkylphenols.

Although heteropoly acids (HPA) and their salts have been known and studied for over 160 years, the interest in their catalytic properties only developed about 20 years ago.

In an article titled "Heterogeneous Catalysis by Heteropoly Compounds of Molybdenum and Tungsten", by M. Misono, Catal. Rev. Sci. Eng., 29. 269 (1987) there is a review of the use of heteropoly acids in synthetic organic chemistry. The heteropolyanions are polymeric oxoanions which are formed by the condensation of more than two different oxoanions (Eq. (1)].

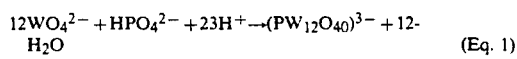

$$12WO_4^{2-} + HPO_4^{2-} + 23H^+ \rightarrow (PW_{12}O_{40})^{3-} + 12 H_2O \quad \text{(Eq. 1)}$$

Polyanions consisting of one kind of oxoanion are called isopolyanions (Eq. (2)].

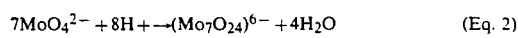

$$7MoO_4^{2-} + 8H^+ \rightarrow (Mo_7O_{24})^{6-} + 4H_2O \quad \text{(Eq. 2)}$$

Acidic elements such as Mo, W, V, Nb and Ta are present as oxoanions in aqueous solutions and polymerize to form polyanions at low pH. The acid forms of these species are called heteropoly and isopoly acids, respectively. A variety of polyanion structures are known. Among these the so-called Keggin structure is a common form which can be represented by $PW_{12}O_{40}^{3-}$, a 12-heteropoly anion $(XM_{12}O_{40})$. The central atom or heteroatom, X, can be P, As, Si, Ge, B, etc. and most of the peripheral atoms, which are called poly or addenda atoms (M), are W or Mo.

The heteropoly compounds display certain advantageous characteristics, among which are the following:
1. The catalyst design is based on acidic and redox properties which can be controlled by the constituent elements of polyanions and counteranions.
2. They can provide a molecular design for solid catalysts, cluster models, or mixed-oxide catalysts.
3. These catalysts provide a unique reaction field.
   a. The Pseudoliquid phase can be studied using spectroscopy, stoichiometry, etc., and changes on the surface are homogeneously magnified through the bulk.
   b. The polyanions are soft bases which stabilize the reaction intermediates in the pseudoliquid phase.

Heteropoly acids are much stronger than the oxoacids of constituent elements and ordinary mineral acids. For example, three protons of the acid forms of $PMo_{12}$ and $PW_{12}$ are completely dissociated in dilute aqueous solutions. The strong acidity is caused by: (1) dispersion of the negative charge over many atoms of the polyanion and (2) the fact that the negative charge is less distributed over the outer surface of the polyanion owing to the double-bond character of the $M=O_t$ bond which polarizes the negative charge of $O_t$ to M.

In organic media, the stepwise dissociation is often observable and the acid strength measured in acetone has been found to show the following order:

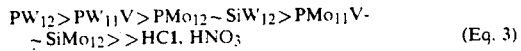
$$PW_{12} > PW_{11}V > PMo_{12} \sim SiW_{12} > PMo_{11}V \sim SiMo_{12} >> HCl, HNO_3 \qquad \text{(Eq. 3)}$$

The acid strengths estimated from the formation constants for complexes of polyanions with chloral hydrate are in the order:

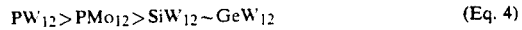
$$PW_{12} > PMo_{12} > SiW_{12} \sim GeW_{12} \qquad \text{(Eq. 4)}$$

The acid strength tends to decrease upon reduction or partial substitution of $Mo^{6+}$ or $W^{6+}$ by $V^{5+}$ owing to an increased negative charge. The thermal stability of the elements constituting a polyanion vary and generally the thermal stability is $W > Mo$ and $P > Si$.

The catalytic function of solid acids is closely related to the acidic properties (amount, strength and type of acid sites) of the catalyst surface. Ibid, p. 287, there is a discussion of five mechanisms which are possibly the origins of acidity.

Though there has been a long history of studies on acid catalysis of heteropoly compounds, it was only recently demonstrated for well-characterized solid heteropoly acids that they are much more active than ordinary solid acids. Catalytic tests reported indicate that heteropoly compounds are efficient for reactions of oxygen-containing molecules (water, ether, alcohol) such as dehydration, etherification, esterification and related reactions at relatively low temperatures. Although they are active for alkylation and transalkylation, it is reported that deactivation during these reactions is significant.

Ibid, p. 291, additional experimental factors are mentioned which show that some catalytic reactions actually proceed in bulk. Further, when heteropoly acids were dispersed on silica gel, the dispersion effect was great in the case of surface-type reaction, but the effect was small for bulk type reaction, although there was less difference at higher temperatures.

In an article titled "Advances in Catalysis by Heteropolyacids," by I. V. Kozhevnikov, Russian Chem. Revs., 56, 811·(1987), there is a discussion of the acid properties of heteropoly acids in solutions and in the solid state, their proton structure and the characteristic features of the homogeneous and heterogeneous acid catalysis.

In the same article there is a review of the description of the Keggin structure, established as early as 1934, and it is noted that it is fairly stable and is preserved in heteropoly acid catalyzed hydration-dehydration and dissolution processes, in substitution reactions of the metal, and in not too extensive oxidation-reduction reactions.

In addition the authors discuss acidic properties of heteropolyacids, including the non-localised hydrated protons and the non-hydrated protons localised at the peripheral oxygen atoms of the polyanion; the nature of the acid centres; the relative acid strengths of the crystalline acids, ibid, p. 814; the dissociation constants of heteropolyacids in water and other solvents; and p. 816, the redox potential of Keggin's structure of heteropoly compounds in aqueous solution.

The HPAs have high Bronsted acidity which is superior to usual acid catalysts and exhibit high stability in the solid state. Tungstic acids are apparently preferred because of their higher acidity, hydrolytic and thermal stability and lower oxidation potentials, in comparison with the molybdenum and vanadium-based acids.

Ibid, p. 817, there is a table of reactions catalysed by heteropoly acids. HPAs are, for example, very active and selective homogeneous catalysts for the decomposition of cumenyl hydroperoxide.

HPA and their salts can also be used as massive and deposited catalysts. In terms of catalytic properties in relation to molecules of polar substances, massive HPA resemble zeolites to some extent. In both cases, virtually all the acid centres of the catalyst are accessible. On p. 821, ibid, it is stated massive HPA's exhibit purely Bronsted acidity. In terms of strength, they are superior to aluminosilicates and, at least in the dehydration of propanol, are much more active than zeolite HY. HPA's have been employed for the industrial synthesis of t-butyl methyl ether from isobutene and methanol, see Ibid. p. 823.

An article by T. Saito in Spec. Chem., 4, pp. 35-6 (1984) focuses on the utilisation of the acid-base and redox characteristics of heteropoly acid catalysts.

An important property of HPA's is their stability. In particular there exists a stable pH region for each anion. Some anions may be converted to a more stable species or decomposed in lower pH regions.

HPAs also exhibit anomalous catalytic activities in various organic synthesis, which suggests not only the contribution of acid-base and redox properties of an inorganic nature but also the existence of interactions between HPAs and organic substrates.

A spectroscopic study on the interaction of HPA anions and proton or organic substrates demonstrates that the HPA anions are too large to be susceptible to solvation and hence can be regarded as a base of low surface charge density. In many catalytic processes involving HPAs, the interaction of the HPA anions with organic substrates as well as protons cannot be ignored.

The effect of supports such as silica, alumina, amorphous aluminosilicate and magnesia on the activity of heteropoly acids for reactions requiring strong and very strong acid sites has been studied and reported in "Catalytic Activity of Supported Heteropoly Acids for Reactions requiring Strong Acid Centres," by K. Nowinska et al., J. Chem. Soc. Faraday Trans., 87, 749 (1991).

In this study there was an attempt to evaluate the effect of different supports on HPA activity for reactions requiring acid centres of different strength. The reaction used in the test was cumene cracking. The most efficient catalyst systems for cumene cracking at 250° C. appeared to be 12-tunstophosphoric acid/$\gamma$-alumina followed by 12-tungstophosphoric acid (HPW)/silica whereas HPW/MgO was inactive. The authors believed their results indicate that the mounting of HPA's on silica and $\gamma$-alumina considerably increased the activity for reactions occurring via a carbonium ion mechanism. On p. 751, ibid, there is a comparison of the catalytic activity and how it is affected by the percentage of loading on the supports.

Of the reactions described in the art which use heteropoly acids as catalysts there does not appear to be any work where homogeneous or heterogeneous HPA's were used in the synthesis of an alkylphenol from phenol and the corresponding olefin. In particular, there is nothing in the art which would suggest the synthesis of nonylphenol with very high selectivities and yields, and high selectivities to desirable para-nonylphenol, under adiabatic conditions using certain heteropoly acids, either solubilized in the nonene/phenol reactants or bonded to suitable oxide supports.

It would be a distinct advance in the art if alkylphenols such as nonylphenols and particularly para-nonylphenols could be prepared in one step with conversion of nonene as high as 91%. It would be particularly desirable if the catalyst exhibited high thermal stability. Such a process would be especially attractive commercially if the system were operated adiabatically, since close temperature control, cooling and recycling make many processes considerably more expensive to build and operate.

It is an object of the instant invention to provide a one-step process for the synthesis of alkylphenols in high yield and with almost complete conversion of olefin using a catalyst system which can operate under adiabatic conditions and exhibits stability even at elevated temperatures. Another object is to obtain high selectivity to desired alkylphenol while, at the same time, producing a high ratio of para- to ortho- alkylphenol products.

SUMMARY OF THE INVENTION

In accordance with the foregoing, the novel method of the instant invention for preparing alkylphenols comprises reacting a phenol with the corresponding olefin in the presence of a catalyst comprising a heteropoly acid, employed as a homogeneous catalyst or deposited on an oxide support at temperatures of from about 60° C. to 250° C.

DESCRIPTION OF THE PREFERRED EMBODIMENT

Preparation of the product of this invention may be carried out typically by reacting the phenol and the olefin under adiabatic conditions. The products demonstrate high selectivities and yields. In the examples where the olefin is nonene, the product is made up of a large ratio of the most desirable form of nonylphenol, para-nonylphenol, compared to ortho-nonylphenol.

The reaction can be represented by the following:

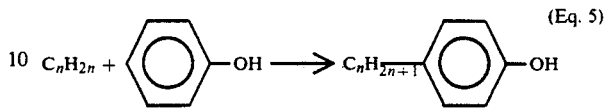
(Eq. 5)

where n is three or greater, preferably in the range 4 to 12.

The olefins which are useful in the instant invention are those which are often available from petrochemical operations. Examples include propylene, 1- and 2-butenes, isobutene and isopentene. Others include isoheptene, diisobutylene, mixed octenes, mixed nonenes, decenes and dodecenes or carbon mixtures thereof. In addition higher straight chain olefins produced by ethylene oligomerization or by dehydrogenation or chlorination-dehydrochlorination of straight chain paraffins are also useful.

Preferred olefins are $C_6$-$C_{12}$ olefins and particularly useful are mixed octenes and mixed nonenes, or mixtures thereof. The examples herein demonstrate the production of p-nonylphenol, which is the preferred form of an important specialty chemical. Nonylphenol is in demand as an intermediate for surfactants, antioxidants and lubricating oil additives.

The molar ratio of the olefin to phenol can vary, but is generally in the ratio of 1:5–5:1. The preferred molar ratio is about 1:1.

The catalysts used to effect this reaction are preferably heteropoly acids. Said heteropoly acids may be bonded to an oxide support, but they may also be solubilized in the reactants or products and used as homogeneous catalysts.

The heteropoly acids which are effective in the subject reaction comprise a class of acids formed by the condensation of two or more inorganic oxyacids. For example, phosphate and tungstate ions, when reacted in an acidic medium, are condensed to form 12-tungstophosphoric acid, a typical heteropoly acid (HPA) according to Equation 6:

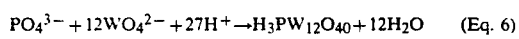
(Eq. 6)

A wide variety of elements ranging from Group I to Group VIII can become the central atom of the HPA anion, or the heteroatom as it is called (P in the case of Eq. 6). The nature of the heteroatom is a governing factor which determines both the condensation structure and the physical properties of the HPA.

Atoms coordinated to the heteroatom via oxygens are called polyatoms (W in the case of Equation 6) and in most cases are any one of such limited species as molybdenum, tungsten, niobium and vanadium. In the case of molybdenum (Mo) as the polyatom, the nature of the heteroatoms, condensation ratios and chemical formulae of the corresponding HPA anions are summarized in Table I.

Anions containing the so-called Keggin structure have a condensation ratio of 1:12 and are the most typical of all HPA anions. Heteropoly acids with the Keggin structure, and their homologues, are generally the most readily available HPA's and the ones most commonly used in catalysis. The synthesis of these HPA's is well documented in the literature [see for example U.S. Pat. No. 3,947,332 (1976)].

TABLE I

Typical heteropolymolybdate anions

| CONDENSATION RATIOS | | HETERO ATOMS (X) | CHEMICAL FORMULAS |
|---|---|---|---|
| 1:12 | Keggin structure | $P^{5+}, As^{5+}, Si^{4+}, Ge^{4+}$ | $[X^{n+}Mo_{12}O_{40}]^{-(8-n)}$ |
| | Silverton structure | $Ce^{4+}, Th^{4+}$ | $[X^{4+}Mo_{12}O_{42}]^{8-}$ |
| 1:11 | Keggin structure (decomposition) | $P^{5+}, As^{5+}, Ge^{4+}, Si^{4+}$ | $[X^{n+}Mo_{11}O_{39}]^{-(12-n)}$ |
| 2:18 | Dawson structure | $P^{5+}, As^{5+}$ | $[X_2^{5+}Mo_{18}O_{62}]^{6-}$ |
| 1:9 | Waugh structure | $Mn^{4+}, Ni^{4+}$ | $[X^{4+}Mo_9O_{32}]^{6-}$ |
| 1:6 | Anderson structure | | |
| | (A type) | $Te^{6+}, I^{7+}$ | $[X^{n+}Mo_6O_{24}]^{-(12-n)}$ |
| | (B type) | $Co^{3+}, Al^{3+}, Cr^{3+}$ | $[X^{n+}Mo_6O_{24}H_6]^{-(6-n)}$ |
| 4:12 | | $As^{5+}$ | $[H_4As_4Mo_{12}O_{52}]^{4-}$ |
| 2:5 | | $P^{5+}$ | $[P_2Mo_5O_{23}]^{6-}$ |

In the case of synthesizing alkylphenols, suitable heteropoly acid catalysts may contain polyatoms selected from the group molybdenum, tungsten, niobium and vanadium, while the heteroatoms may be phosphorus, silicon, germanium, and arsenic. Preferably the heteroatoms are phosphorus or silicon. These heteropoly acids would likely have the Keggin structure, $H_{8-n}[XM_{12}O_{40}]$, where X=P or Si, M=Mo or W and n is an integer which is 4 or 5.

The preferred heteropoly acids for the practice of this invention include 12-molybdophosphoric acid, $H_3PMo_{12}O_{40}$, 12-tungstophosphoric acid, molybdosilicic acid, $H_4SiMo_{12}O_{40}$ and 12-tungstosilicic acid. Said acids are generally used as heterogeneous catalysts bonded to a suitable support.

The support should preferably comprise an inert compound. Compounds which may be employed are those containing elements of Group III and IV of the Periodic Table. Suitable compounds include the oxides of aluminum, silicon, titanium and zirconium or combinations thereof, e.g. alumina, silica (silicon dioxide), titania (titanium dioxide) and zirconia. Also suitable are carbon, ion-exchange resins, carbon-containing supports and silica-alumina clays including the montmorillonite clays. Good results were observed using $TiO_2$ as the support.

The inert support may be in the form of powders, pellets, spheres, shapes and extrudates. As will be demonstrated by the examples, the supports are preferably of high purity and high surface area.

The weight percent of heteropoly acid to Group III/Group IV oxide support should be such that the concentration of the polyatom (Mo, W, Nb or V) in the formulated catalyst is in the range of 0.1 wt % to 30 wt %, although concentrations outside this range may also be employed. Where the heteropoly acid is, for example, 12-molybdophosphoric acid, supported on titania, a suitable quantity of molybdenum is 1–20 wt %. In the preparation of a tungstophosphoric acid-on-titania catalyst, on the other hand, the tungsten content may be 1–30 wt %.

Preparation of alkylphenols is conducted in a fixed bed, continuous flow reactor.

The reaction is conducted under adiabatic conditions. The "hot spot" or maximum temperature of the reactor can be in the range of 60°–250° C. and preferably 80° C. to 140° C. The preferred temperature depends on the choice of reactants, however, in the case of nonene and phenol an effective temperature is about 90° C. The pressure can be in the range of atmospheric to 500 psi and is preferably about 100 psi.

Typically the alkylphenol is generated continuously in up to ca. 70+ wt % concentration in the crude product liquid effluent.

Olefin conversions are high. Nonenes conversion is as high as 91%. Preferably the nonenes conversion is >80% and the para-nonylphenol to ortho-nonylphenol weight ratio is >10.

These yields are achieved at a total liquid hourly space velocity (LHSV) of one to 10 under mild conditions.

Here LHSV is defined as follows:

$$LHSV = \frac{\text{Weight of Total Liquid Feed Run Through the Reactor Per Hour}}{\text{Volume of Catalyst in Reactor}}$$

Conversion of olefins (wt %) is estimated in the following examples using the equation:

$$100 - \left(\frac{\text{Wt \% Conc. of Olefin in Product}}{\text{Wt \% Conc. of Olefin in Feed}}\right) \times 100$$

Yields of alkylphenol (mole %) are estimated from:

$$\frac{\text{Moles of Alkylphenyl in Product Liquid}}{\text{Moles of Olefin in Feed}} \times 100$$

The accompanying Examples illustrate:
1) The synthesis of nonylphenol from phenol/nonene mixtures (Ex. 3) using the 12-tungstophosphoric acid catalyst of Ex. 1, where:
   a) 91% nonenes conversion per pass is achieved at 120°, LHSV 1.
   b) The p-nonylphenol to o-nonylphenol weight ratio reaches 15.7 at 80° C.
   c) The nonylphenol to dinonylphenol weight ratio is 6.2 at 120° C.
   d) 79% nonenes conversion is achieved per pass at 100° C., LHSV 3.
2) The synthesis of nonylphenol from phenol/nonene in Ex. 4 using the 12-molybodphosphoric acid catalyst of Ex. 2, where:
   a) P-Nonylphenol to o-nonylphenol weight ratio is 13.2 at 120° C.
   b) Nonylphenol to dinonylphenol ratio climbs to 16.3 at 100° C., LHSV 3.
3) In general, this class of heteropoly acid catalyst can provide:
   a) High nonene conversions per pass (Ex. 3).

b) High total nonylphenol concentrations in the crude product (Ex. 3).
c) High p-nonylphenol to o-nonylphenol ratios (Ex. 3 and 4)
d) High total nonylphenol to dinonylphenol ratios (Ex. 4).
e) Good performance at high LHSV's (Ex. 3).
4) The generation of nonylphenol from phenol/nonene using 12-tungstophosphoric acid as a homogeneous catalyst (Ex. 5).

EXAMPLE 1

This Example illustrates the preparation of a 12-tungstophosphoric acid-on-titania catalyst.

A solution of 12-tungstophosphoric acid (320 g) in distilled water (1 liter) was added, with stirring, to 1000 cc of HSA titania carrier extrudates (from Norton Company, #64733, ⅛" diameter extrudates, surface area ca. 60 m²/g). The liquid was absorbed into the extrudates, with stirring, for 24 hours. The mixture was then rotary evaporated to remove excess liquid and calcined at 150°-350° C. under slow nitrogen flow conditions.

Weight of recovered white extrudates:
1200 g
Analysis showed the presence of:
W = 16.7%
P = 0.24%
$H_2O$ = 0.06%
Acidity = 0.25 meq/g

EXAMPLE 2

This example illustrates the preparation of a 12-molybdophosphoric acid-on-titania catalyst.

A solution of 12-molybdophosphoric acid (320 g) in distilled water 1 liter) was added, with stirring, to 1000 cc of HSA titania carrier extrudates (from Norton Company, #9165004, ⅛" extrudates, surface area 48 m²/g). The liquid was absorbed into the extrudates, with stirring, for 24 hours. The mixture was then rotary evaporated to remove excess liquid and calcined at 150° to 350° C. in a stream of nitrogen.

Weight of recovered yellow extrudates:
1139 g
Analyses showed the presence of:
Mo = 10.5%
$H_2O$ = 0.9%
Acidity = 0.40 meq/g

EXAMPLE 3

This Example illustrates the selective production of para-nonylphenol from phenol and mixed nonene using a 12-tungstophosphoric acid-on-titania catalyst.

Synthesis was conducted in a 500 cc capacity, tubular reactor constructed of stainless steel, operated upflow and fitted with temperature, pressure and flow rate regulating devices.

The reactor was charged at the beginning of the experiment with 400 cc of the 12-tungstophosphoric acid-on-titania of Example 1 and a screen of glass wool was placed at the top and bottom of the reactor to ensure the catalyst would remain in the middle portion.

Said catalyst bed was treated with a phenol/nonene mix (1:1 weight ratio, 1.34:1 molar ratio) upflow, at a rate of 400 cc/hr, while the first section of the catalyst bed was held at 80° C. The reactor was run adiabatically and the hot spot temperature along the catalyst bed was at least 95° C.; total pressure was 100 psi. Samples of crude product effluent were collected after the unit had reached steady-state conditions and analyzed by glc and lc, Typical analyses data are given in Table 2.

The experiment was repeated at a series of temperatures (100, 120° C.) and flow rates (800, 1200 cc/hr) under adiabatic conditions. These run and results data are also given in Table 2. Typical calculated nonene conversion levels and nonylphenol/dinonylphenol product weight ratios are given in Table 3.

TABLE 2

| | | | | NONYLPHENOL SYNTHESES | | | | | | | | |
|---|---|---|---|---|---|---|---|---|---|---|---|---|
| | | PhOH/C₉⁻ | CONTROL | FEED | | PRODUCT COMPOSITION (%)ᵃ | | | | | | HOT SPOT |
| | | MOLAR | TEMP | RATE | | ←—g/c—→ | | | | ←—lc—→ | | TEMP |
| EX. | CATALYST | RATIO | (°C.) | (cc/hr) | SAMPLE | C₉⁻ | PhOH | NP | DNP | DNP | o-NP | p-NP | (°C.) |
| 3 | Ex. 1 | 1.34 | | | FS-1 | 50.1 | 49.9 | | | | | | |
| | | | 80 | 400 | 1 | 10.6 | 24.9 | 54.7 | 9.6 | 16.6 | 4.8 | 75.4 | 95 |
| | | | 100 | 400 | 2 | 3.8 | 20.8 | 64.0 | 11.2 | 17.6 | 4.9 | 75.2 | 111 |
| | | | 120 | 400 | 3 | 4.3 | 21.4 | 63.3 | 10.2 | 18.2 | 6.5 | 73.0 | 130 |
| | | | 100 | 800 | 4 | 8.2 | 26.0 | 55.3 | 10.3 | 17.8 | 5.3 | 74.4 | 108 |
| | | | 100 | 1200 | 5 | 10.4 | 28.8 | 51.4 | 9.3 | 18.1 | 6.0 | 73.1 | 110 |

ᵃDesignations: Nonene, C₉⁻: Phenol, PhOH, Total Nonylphenol, NP, Dinonylphenol, DNP, ortho-nonylphenol, o-NP, Para-nonylphenol, p-NP.

TABLE 3

| | | NONYLPHENOL PRODUCT ANALYSES DATA | | | | | |
|---|---|---|---|---|---|---|---|
| | | CONTROL | | NONENE | NP | WEIGHT RATIO | |
| EX. | SAMPLE | TEMP (°C.) | LHSV | CONV. (%) | CONC. (%) | p-NP/o-NP | NP/DNP |
| 3 | 1 | 80 | 1 | 79 | 55 | 15.7 | 5.7 |
| | 3 | 120 | 1 | 91 | 63 | 11.2 | 6.2 |
| | 5 | 110 | 3 | 79 | 51 | 12.2 | 5.5 |

EXAMPLE 4

This Example illustrates the selective production of para-nonylphenol from phenol and mixed nonenes using a 12-molybdophosphoric acid-on-titania catalyst.

Syntheses was conducted in the same 500 cc capacity, tubular reactor of Example 3 using the same procedures. The reactor was charged with 400 cc of the 12-molybdophosphoric acid-on-titania of Example 2 and said catalyst bed was treated with phenol/nonene mix (1:1 weight ratio, 1.34:1 molar ratio) at a series of temperatures (80°-120° C.) and flow rates (400-1200 cc/hr) typical samples analyses are given in Table 4. Calculated nonene conversion levels and nonylphenol/dinonylphenol product weight ratios are given in Table 5.

TABLE 4

| | | | | | | NONYLPHENOL SYNTHESES | | | | | | | |
|---|---|---|---|---|---|---|---|---|---|---|---|---|---|
| | | PhOH/C9- | CONTROL | FEED | | PRODUCT COMPOSITION (%) | | | | | | | HOT SPOT |
| | | MOLAR | TEMP | RATE | | ←g/c→ | | | | ←lc→ | | | TEMP |
| Ex. | CATALYST | RATIO | (°C.) | (cc/hr) | SAMPLE | C9- | PhOH | NP | DNP | DNP | o-NP | p-NP | (°C.) |
| 4 | Ex. 2 | 1.34 | | | FS-1 | 50.1[b] | 49.2[b] | | | | | | |
| | | | 80 | 400 | 1 | 39.6 | 33.4 | 25.2 | 1.9 | 7.1 | 7.5 | 78.1 | 86 |
| | | | 100 | 400 | 2 | 31.3 | 36.7 | 29.6 | 2.4 | 7.8 | 6.7 | 78.8 | 103 |
| | | | 120 | 400 | 3 | 26.0 | 33.5 | 36.9 | 3.6 | 9.2 | 6.0 | 79.2 | 120 |
| | | | 100 | 800 | 4 | 36.1 | 39.4 | 22.9 | 1.6 | 6.8 | 6.4 | 79.6 | 108 |
| | | | 100 | 1200 | 5 | 34.0 | 38.2 | 26.1 | 1.6 | 6.4 | 6.6 | 81.0 | 132 |

TABLE 5

| | | NONYLPHENOL PRODUCT ANALYSES DATA | | | | | |
|---|---|---|---|---|---|---|---|
| | | CONTROL | | NONENE | NP | WEIGHT RATIO | |
| EX. | SAMPLE | TEMP (°C.) | LHSV | CONV. (%) | CONC. (%) | p-NP/o-NP | NP/DNP |
| 4 | 1 | 80 | 1 | 21 | 25 | 10.4 | 13.3 |
| | 3 | 120 | 1 | 48 | 37 | 13.2 | 10.3 |
| | 5 | 100 | 3 | 32 | 26 | 12.3 | 16.3 |

EXAMPLE 5

This example illustrates the synthesis of nonylphenol from phenol plus mixed nonenes using a solubilized heteropoly acid catalyst.

A mix of phenol (85.0 g, 0.90 mole), nonene (85.0 g, 0.67 mole) and 12-tungstophosphoric acid (1.25 g) solubilized in 10 ml of distilled water, was charged to a glass-lined, 850 cc capacity reactor, fitted with temperature and pressure controls. Said reactor was then flushed with nitrogen, heated to 100° C. with agitation, held at temperature for 4 hours, and then allowed to cool.

The recovered product liquid comprised two layers. The water-white, lighter phase (78 ml) was found, by glc analyses, to contain 4.7% nonylphenol and 0.1% dinonylphenol. The heavier, red-colored, phase (116 ml) contained 3.6% nonylphenol.

What is claimed is:

1. A one-step method for selective synthesis of para-nonylphenol which comprises reacting phenol with mixed nonenes under adiabatic conditions in the presence of a catalyst consisting essentially of a heteropoly acid from the group consisting of 12-tungstophosphoric acid, 12-tungstosilicic acid and 12-molybdosilicic acid, supported on an inert oxide selected from the group consisting of titanium dioxide, alumina and silica, as well as mixtures thereof, at a temperature of from 60° C. to 250° C. and a pressure of near atmospheric to about 500 psi.

2. The method of claim 1 wherein the heterogeneous catalyst comprises 0.1 to 30% by weight of polyatom (M=Mo or W) on the inert supports.

3. The method of claim 1 wherein the catalyst comprises 12-tungstophosphoric acid on a titania support.

4. The method of claim 1 wherein the catalyst comprises 12-molybdophosphoric acid on a titania support.

5. The method of claim 1 wherein the maximum operating temperature is in the range from 80° to 140° C.

6. The method of claim 1 wherein the nonenes to phenol molar feed ratio is from 1:5 to 5:1.

7. The method of claim 6 wherein the nonenes conversion is >80% and the para-nonylphenol to ortho-nonylphenol weight ratio is >10.

* * * * *